(12) United States Patent
Beebe et al.

(10) Patent No.: US 12,359,156 B2
(45) Date of Patent: Jul. 15, 2025

(54) PLATFORM AND METHOD FOR TESTING ANTIBIOTIC SENSITIVITY OF A POLYMICROBIAL INFECTION

(71) Applicants: David J. Beebe, Monona, WI (US); Layla J. Barkal, Madison, WI (US); Jason Yu, Madison, WI (US)

(72) Inventors: David J. Beebe, Monona, WI (US); Layla J. Barkal, Madison, WI (US); Jason Yu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 18/131,620

(22) Filed: Apr. 6, 2023

(65) Prior Publication Data

US 2023/0242856 A1 Aug. 3, 2023

Related U.S. Application Data

(62) Division of application No. 16/217,588, filed on Dec. 12, 2018, now Pat. No. 11,725,172.

(51) Int. Cl.
*C12M 1/32* (2006.01)
*C12M 3/06* (2006.01)
*C12Q 1/18* (2006.01)

(52) U.S. Cl.
CPC ............ *C12M 23/16* (2013.01); *C12M 23/12* (2013.01); *C12Q 1/18* (2013.01)

(58) Field of Classification Search
CPC .......... C12M 23/16; C12M 23/12; C12Q 1/18
See application file for complete search history.

(56) References Cited

U.S. PATENT DOCUMENTS 6,703,247 B1 * 3/2004 Chu ...................... C12Q 1/686
422/536
2005/0048599 A1 3/2005 Goldberg
(Continued)

FOREIGN PATENT DOCUMENTS

KR 101782263 B1 * 9/2017

OTHER PUBLICATIONS

Shahidi et al., "Effect of Mixed Cultures on Antibiotic Susceptibility Testing", Applied Microbiology, Nov. 1696 p. 766-770.
(Continued)

*Primary Examiner* — Liban M Hassan
(74) *Attorney, Agent, or Firm* — Boyle Fredrickson, S.C.

(57) ABSTRACT

A platform and method for testing antibiotic sensitivity of a polymicrobial infection is provided. The platform includes a body defining a plurality of sets of chambers and a plurality of wells. Each set of chambers has a plurality of chambers adapted for culturing microbes of the polymicrobial infection therein. Each well is associated with a corresponding set of chambers and has an input in fluidic communication with the outlets of the plurality of chambers in the corresponding set of chambers. Selected antibiotic therapies may be received in the wells which fluidically connect the plurality of chambers in a corresponding set of chambers such that microbes cultured in the plurality of chambers in the corresponding set of chambers are in soluble factor contact.

10 Claims, 7 Drawing Sheets

(56) References Cited

U.S. PATENT DOCUMENTS

| | | | |
|---|---|---|---|
| 2007/0231887 A1* | 10/2007 | McGrath | C12M 29/04 |
| | | | 435/297.5 |
| 2008/0299649 A1* | 12/2008 | Martin | C12M 23/38 |
| | | | 435/297.1 |
| 2009/0155920 A1 | 6/2009 | Carlson | |
| 2014/0256032 A1 | 9/2014 | Wooder | |
| 2016/0002583 A1 | 1/2016 | Hlinka | |

OTHER PUBLICATIONS

Mohan et al., "A microfluidic approach to study the effect of bacterial interactions on antimicrobial susceptibility in polymicrobial cultures", RSC Adv., 2015, 5, 35211.

Maurer et al., "Advances in rapid identification and susceptibility testing of bacteria in the clinical microbiology laboratory: implications for patient care and antimicrobial stewardship programs", Infectious Disease Reports 2017, vol. 9: 6839.

De Vos et al., "Interaction networks, ecological stability, and collective antibiotic tolerance in polymicrobial infections", PNAS, Oct. 3, 2017, vol. 114, No. 40 pp. 10666-10671.

Kim et al., "Defined spatial structure stabilizes a synthetic multispecies bacterial community", PNAS, Nov. 25, 2008, vol. 105, No. 47, pp. 18188-18193.

Chung et al., "Simultaneous and quantitative monitoring of co-cultured Pseudomonas aeruginosa and *Staphylococcus aureus* with antibiotics on a diffusometric platform", Scientific Reports, published Apr. 12, 2017, 7:46336, 12 pages.

\* cited by examiner

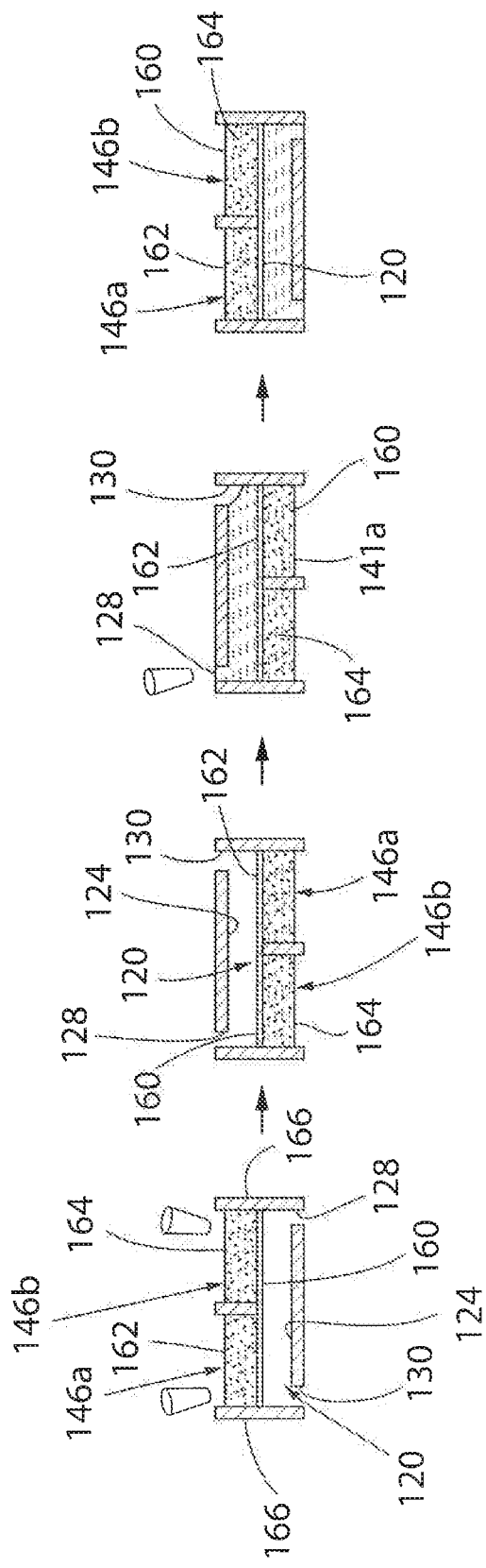

PLATFORM AND METHOD FOR TESTING ANTIBIOTIC SENSITIVITY OF A POLYMICROBIAL INFECTION

CROSS-REFERENCE TO RELATED APPLICATION

This application is a divisional of U.S. patent application Ser. No. 16/217,588; filed on Dec. 12, 2018; entitled "Platform And Method For Testing Antibiotic Sensitivity Of A Polymicrobial Infection Rolled Label Web Releasably Attached to a Core"; the content of which is incorporated herein by reference in its entirety.

FIELD OF THE INVENTION

This invention relates generally to antibiotic sensitivity testing, and in particular, to a platform and method for testing antibiotic sensitivity of a polymicrobial infection by culturing multiple bacterial strains in soluble-factor communication with each other.

BACKGROUND AND SUMMARY OF THE INVENTION

Early microbiology studies are primarily based on adaptations of a one microbe, one disease hypothesis, known as Koch's postulates, introduced in the late 1800s. Koch's postulates states that a disease causing microbe should have the following four criteria: 1) the microbe must be found in all organisms affected from the disease, but not in healthy organisms; 2) the microbe must be isolatable from the disease affected organism and also grown in pure culture; 3) the pure cultured microbe should be able to cause the same disease when introduced into a healthy organism; and 4) the microbe must be able to be isolated from the infected organism and be identical to the original isolated strain. More recently, however, researchers have realized that microbes do not exist as single entities, but as complex multispecies communities in the majority of environments ranging from soil to the gastrointestinal tract of animals. These multi-microbial species interactions play a significant role in human health and pathology. For instance, the human gut alone has an estimated 500 to 1000 different microbial species. Different members within the microbial community interact locally in ways that can affect the dynamics and stability of the population as a whole. The role of these interactions in human health and pathology has recently emerged, with various studies showing that microbial communities inhabiting the gut play a critical role in human pathologies like diabetes, obesity, Parkinson's, Alzheimer's, and even cancers.

Recent advances in both throughput and cost reduction in metagenomic sequencing technologies have enabled the study of microbiomes and their participating members with unprecedented throughput and offer insight into a more systems-level understanding of the identities of microbial community members. Despite progress in these areas, much remains to be understood regarding how the individual members of a community interact with their adjacent neighbors and the physiological functions that arise from these interactions within their microenvironment. Multi-variable combinatorial screening is a universal critical step in the development of combinatorial drug treatments, stem cell differentiation, studying cell-cell/microbe interactions, among many other applications involving multi-parameter experimental optimization.

Current standard technologies for studying microbial communities include 16S ribosomal RNA (rRNA) sequencing, fluorescence in situ hybridization (FISH), macroscale (mostly pairwise) co-cultures, and computer-based modeling. 16S rRNA sequencing can provide valuable information regarding which microbial species are present within a community, but cannot elucidate what interactions occur between which members of the community. FISH can provide information regarding the spatial distribution of different microbial species within a sample, but cannot infer functional readouts, is challenging to perform and is also limited to the number of fluorescent probes and wavelengths available. Pairwise co-cultures are generally performed in conventional laboratory culture vessels like multi-well plates, tubes, and solid agar plates. Although suitable for small scale interaction screens for a handful of communities, the process is ill suited for taking on the colossal task of screening and re-assembling the vast parameter space of interactions for even small numbers of microbial species. Additionally, macroscale liquid cultures are prone to disturbance by convective flow, causing rapid mixing and dilution of localized diffusible factors. As a result, valuable local interaction phenotypes could be lost. Computer based modeling is useful for gaining understanding of how competition and cooperation within a microbial community can maintain stability, survival, and biodiversity, such as "rock—paper—scissors" interaction dynamics, and fills some of the gaps in current experimental limitations in screening multi-species interactions. However, the results obtained from modeling biological systems is highly hypothetical and often not translatable to real-world conditions.

In view of the foregoing, it is evident that there exists a significant need for practical microscale co-culture tools with sufficient throughput to allow for large scale screening of microbial community interactions at the microscale. This is a critical piece of the puzzle to enable scientists to gain functional insight and understanding of how different community members interact and drive community behavior within the microenvironment. Development of microscale co-culture tools with sufficient throughput to allow for large scale screening of microbial community interactions at the microscale could lead to important insights into future clinical treatment strategies. For example, studies have shown that microbes in co-cultures can exhibit differing responses to antibiotic treatment compared to those in isolation, in which the microbial members in cohabitation can either antagonize or potentiate antibiotic susceptibility to the whole community. Hence, in the context of polymicrobial infection, interplay between two or more invading pathogens is likely clinically significant and unfortunately, unaccounted for with current methods.

Heretofore, patients found to have an infection undergo antibiotic sensitivity testing performed on their specific bacterial pathogens. This type of testing helps clinicians select antibiotic therapy in a patient-specific manner. Unfortunately, antibiotic sensitivity testing can be a poor predictor of patient outcome. For example, in the phase 3 clinical trial for cefotaxime, a "sensitive" test result, in the best case scenario, meant 93% of patients would respond. Importantly, 64% of patients who had a "resistant" test result also responded to the antibiotic therapy. Both sources of error are clinically significant. Clinicians want to treat patients with antibiotics that are effective and also provide good antimicrobial stewardship by avoiding jumping to backup/reserve antibiotics if other, more frequently used options, would also be effective.

There are a number of factors that contribute to the poor predictive value of state of the art antibiotic sensitivity tests, most of which come back to the fact that the assay is oversimplified; it is performed on pure bacterial isolates. It neglects the role of both the patient's immune system and the role other nearby pathogens may play. In the context of polymicrobial infection, interplay between two or more invading pathogens is likely clinically significant and unfortunately, unaccounted for with current methods.

Therefore, it is a primary object and feature of the present invention to provide a platform and method for testing antibiotic sensitivity of a polymicrobial infection by culturing multiple bacterial strains in soluble-factor communication with each other.

It is a further object and feature of the present invention to provide a platform and method for testing antibiotic sensitivity of a polymicrobial infection that provides a large number of combinations with high throughput within a small scale to allow for detection of diffusion-limited interaction events.

It is a still further object and feature of the present invention to provide a platform and method for testing antibiotic sensitivity of a polymicrobial infection that possesses a simple and high content data readout.

It is a still further object and feature of the present invention to provide a platform and method for testing antibiotic sensitivity of a polymicrobial infection that is scalable in terms of both number of different members in combination and cell number of each member.

It is a still further object and feature of the present invention to provide a platform and method for testing antibiotic sensitivity of a polymicrobial infection that is simple and straightforward to operate and that enables the sufficient long-term culture of specific target microbes.

In accordance with the present invention, a platform for testing antibiotic sensitivity of a polymicrobial infection is provided. The platform includes a body defining a plurality of chambers having outlets and a well having an input. Each chamber is adapted for receiving a corresponding microbe of the polymicrobial infection therein. The well is in fluidic communication with the outlets of the plurality of chambers and is well adapted for receiving a selected antibiotic therapy therein. The selected antibiotic therapy received in the well fluidically connects each of chambers such that microbes received in the plurality of chambers are in soluble factor contact.

The body further includes a permeable membrane disposed between the outlets of the plurality of chambers and the input of the well. Preferably, the permeable membrane is a porous polycarbonate membrane. The body also includes upper and lower surfaces.

Each of the plurality of chambers has an opening communicating with the upper surface of the body. The well is partially defined by a closed surface within the body. The closed surface is generally parallel to the lower surface of the body. A well inlet extends between the closed surface of the well and the lower surface of the body. The well inlet allows for access to the well for loading the selected antibiotic therapy therein. An air outlet also extends between the closed surface of the well and the lower surface of the body. The air outlet allows for the purging of air from the well during the loading of the selected antibiotic therapy therein.

In accordance with a further aspect of the present invention, a platform for testing antibiotic sensitivity of a polymicrobial infection is provided. The platform includes a body defining a plurality of sets of chambers and a plurality of wells. Each set of chambers has a plurality of chambers adapted for receiving microbes of the polymicrobial infection therein. Each well is associated with a corresponding set of chambers. An input of the well is in fluidic communication with the outlets of the plurality of chambers in the corresponding set of chambers. Each well is adapted for receiving a selected antibiotic therapy wherein the selected antibiotic therapy received in the well fluidically connects the plurality of chambers in the corresponding set of chambers such that microbes received in the plurality of chambers in the corresponding set of chambers are in soluble factor contact.

The body further includes a permeable membrane disposed between the outlets of the plurality of chambers of the plurality of sets of chambers and the inputs of corresponding wells of the plurality of wells. The permeable membrane is a porous polycarbonate membrane. The body includes upper and lower surfaces. Each of the plurality of chambers of the plurality of sets of chambers has an opening communicating with the upper surface of the body. Each well of the plurality of wells is partially defined by a closed surface within the body. The closed surface of each well is generally parallel to the lower surface of the body.

The body further includes a plurality of well inlets and a plurality of air outlets. Each well inlet extends between the closed surface of a corresponding well and the lower surface of the body and allows access to the corresponding well for loading the selected antibiotic therapy therein. Each air outlet extends between the closed surface of the corresponding well and the lower surface of the body and allows for the purging of air from the corresponding well during the loading of the selected antibiotic therapy therein.

In accordance with a still further aspect of the present invention, a method for testing antibiotic sensitivity of a polymicrobial infection is provided. The method includes the steps of providing microbes of the polymicrobial infection in corresponding chambers of a plurality of chambers and loading a selected antibiotic therapy in a well so as to fluidically connect each of chambers such that microbes provided in the plurality of chambers are in soluble factor contact. The interaction of the selected antibiotic therapy and the microbes is then observed.

A permeable membrane may be positioned between outlets of the plurality of chambers and an input to the well. The permeable membrane is a porous polycarbonate membrane. Each of the plurality of chambers has an opening communicating with the atmosphere and the well is interconnected to the atmosphere with a well inlet. The well inlet allows for access to the well for loading the selected antibiotic therapy therein. The well may also be interconnected to the atmosphere with an air outlet. The air outlet allows for the purging of air from the well during the loading of the selected antibiotic therapy therein.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 9a is a cross-sectional view of the first layer of the microfluidic device taken along line 9a-9a of FIG. 8a;

FIGS. 12a-12d are a plurality of schematic views showing sequential steps performed with the platform of FIG. 6 to effectuate the methodology of the present invention.

DETAILED DESCRIPTION OF THE DRAWINGS

Figure 1:
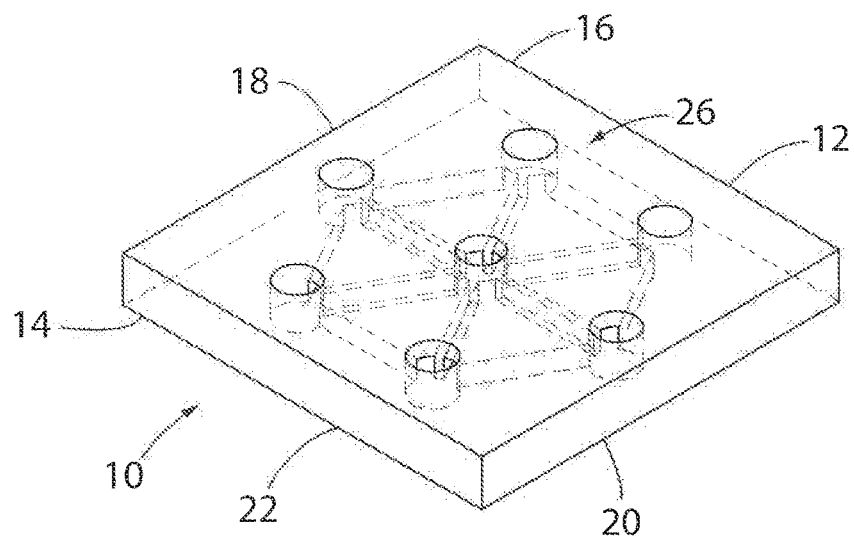
FIG. 1 is an isometric view of a microfluidic device including a platform for effectuating a method in accordance with the present invention.
Figure 2:
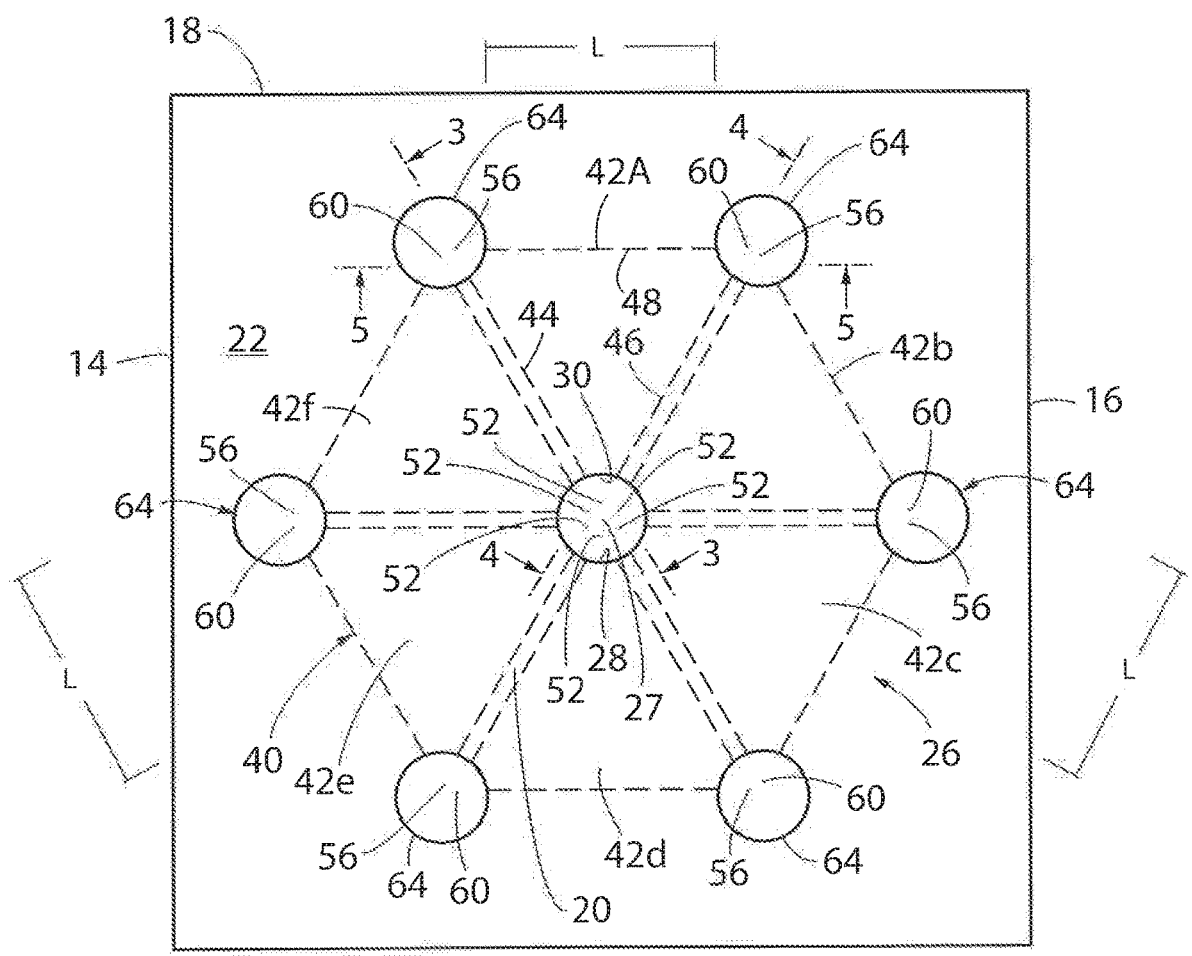
FIG. 2 is a top plan view of the platform of FIG. 1.

Referring to FIGS. 1-2, a microfluidic device in accordance with the present invention is generally designated by the reference numeral 10. Microfluidic device 10 may be formed from polystyrene (PS) or polydimethylsiloxane (PDMS), however, other materials are contemplated as being within the scope of the present invention. In the depicted embodiment, microfluidic device 10 includes base 12 having first and second ends 14 and 16, respectively, and first and second sides 18 and 20, respectively. First and second ends 14 and 16, respectively, and first and second sides 18 and 20, respectively, of base 12 define the outer periphery of base 12. The outer periphery of base 12 interconnects upper and lower surfaces 22 and 24, respectively.

Figure 3:
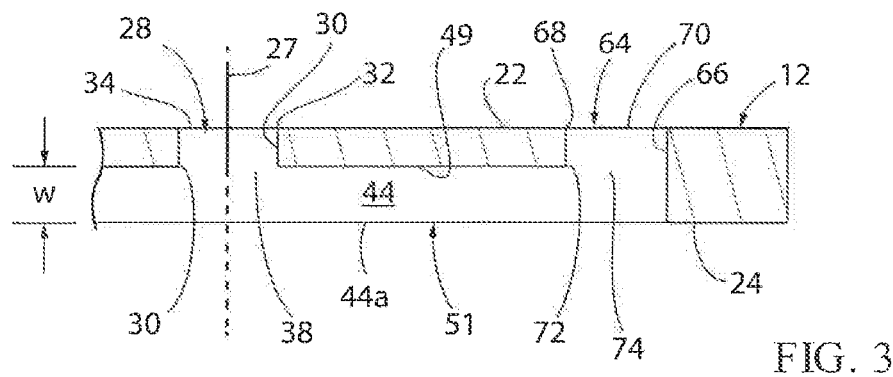
FIG. 3 is a cross-sectional view of the platform taken along line 3-3 of FIG. 2.
Figure 4:
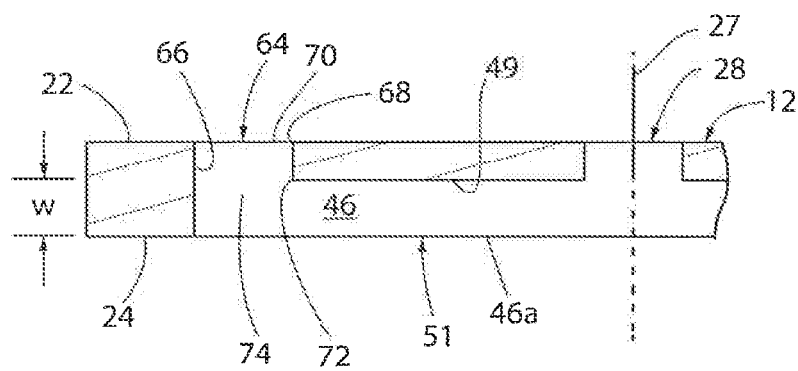
FIG. 4 is a cross-sectional view of the platform taken along line 4-4 of FIG. 2.

As hereinafter described, microfluidic device 10 defines platform 26 for effectuating a method of multi-variable combinational screening is accordance with the present invention. It is noted that microfluidic device 10 may include additional platforms 26 provided therein for effectuating the methodology in after described, without deviation from the scope of the present invention. Referring to FIGS. 2-4, in the depicted embodiment, platform 26 includes a vertical common well 28 extending along a corresponding axis 27 into base 12 from upper surface 22 thereof. Common well 28 is defined by a generally cylindrical side wall 30 having an upper edge 32 intersecting upper surface 22 of base 12 so as to define opening 34. Lower edge 36 of side wall 30 defines outlet 38 of common well 28.

Platform 26 further includes an array of multiplexing chambers 40 extending radially outward from axis 27 and communicating with exit 38 of common well 28. In the depicted embodiment, six (6), generally triangular multiplexing chambers 42a-42f are provided in base 12. As hereinafter described, each multiplexing chamber 42a-42f is identical in structure and configuration. As such, the following description of multiplexing chamber 42a is understood to describe multiplexing chambers 42b-42f as if fully described herein.

Multiplexing chamber 42a is generally triangular in shape and is defined by first sidewall 44 lying in a first plane, a second sidewall 46 lying in a second plane and third sidewall 48 lying in a third plane. First, second and third sidewalls 44, 46 and 48, respectively, depend from upper, generally planar, chamber surface 49 and intersect lower surface 24 of base 12 at corresponding lower terminal edges 44a, 46a and 48a, respectively. It can be appreciated that lower edges 44a, 46a and 48a of first, second and third sidewalls 44, 46 and 48, respectively, lie in a common plane with lower surface 24 of base 12 and define opening 51. First, second and third sidewall 44, 46 and 48, respectively, have a common width and, for reasons hereinafter described, first, second and third sidewall 44, 46 and 48, respectively, have a generally equal length L. Hence, multiplexing chamber 42a has an equilateral triangular configuration. The first and second planes, respectively, are provided at an angle of approximately 60 degrees to each other and intersect each other along a line, thereby defining first vertex 52 of the triangular configuration of multiplexing chamber 42a. It can be appreciated that first vertex 52 is adjacent to axis 27. Similarly, the first and third planes, respectively, are provided at an angle of approximately 60 degrees to each other and intersect each other along a line, thereby defining second vertex 56 of the triangular configuration of multiplexing chamber 42a. Second and third planes, respectively, are provided at an angle of approximately 60 degrees to each other and intersect each other along a line, thereby defining third vertex 60 of the triangular configuration of multiplexing chamber 42a.

As best seen in FIG. 2, it understood that second vertex 56 of each multiplexing chamber 42a-42f is adjacent to third vertex 60 of an adjacent multiplexing chamber 42a-42f. In other words, second vertex 56 of multiplexing chamber 42a is adjacent to third vertex 60 of adjacent multiplexing chamber 42f; second vertex 56 of multiplexing chamber 42f is adjacent to third vertex 60 of adjacent multiplexing chamber 42e; second vertex 56 of multiplexing chamber 42e is adjacent to third vertex 60 of adjacent multiplexing chamber 42d; second vertex 56 of multiplexing chamber 42d is adjacent to third vertex 60 of adjacent multiplexing chamber 42c; second vertex 56 of multiplexing chamber 42c is adjacent to third vertex 60 of adjacent multiplexing chamber 42b; and second vertex 56 of multiplexing chamber 42b is adjacent to third vertex 60 of adjacent multiplexing chamber 42a.

Figure 5:
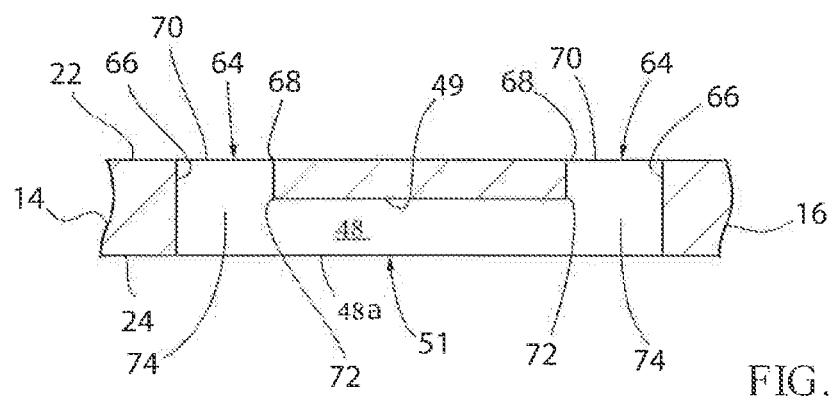
FIG. 5 is a cross-sectional view of the platform taken along line 5-5 of FIG. 2.
Figure 6:
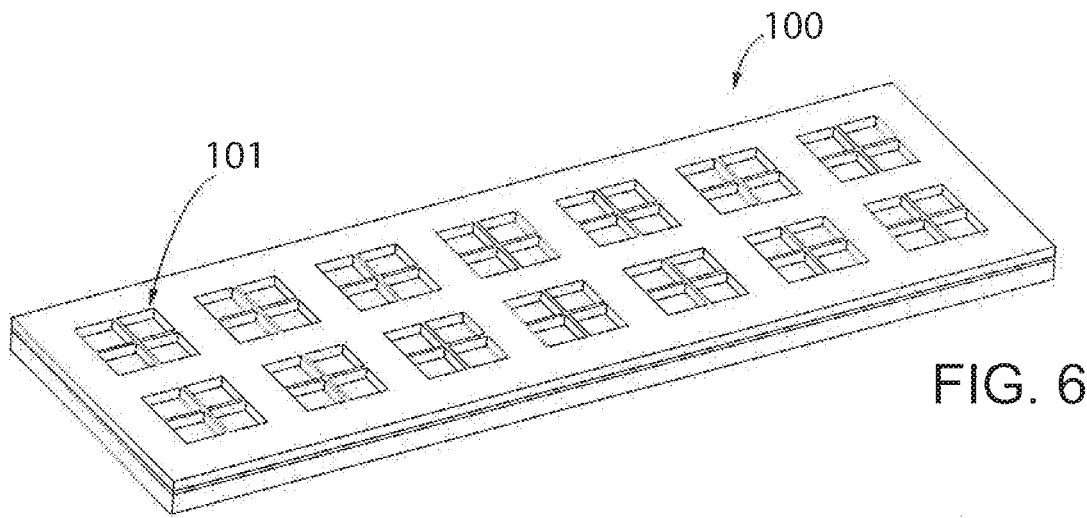
FIG. 6 is an isometric view of an alternate embodiment of a microfluidic device including a plurality of platforms for effectuating a method in accordance with the present invention.

Platform 26 further includes a plurality of variable wells 64 provided in base 12. Variable wells 64 extend into base 12 from upper surface 22 thereof along corresponding axes at a location which overlaps second vertices 56 of each multiplexing chamber 42a-42f (e.g. multiplexing chamber 42a) and third vertices 60 of the multiplexing chamber 42a-42f adjacent thereto (e.g. multiplexing chamber 42f). As best seen in FIGS. 3-5, each variable well 64 is defined by a generally cylindrical side wall 66 having an upper edge 68 intersecting upper surface 22 of base 12 so as to define opening 70. Lower edge 72 of side wall 66 of each variable well 64 defines an outlet 74 having sufficient diameter to communicate with two adjacent multiplexing chambers 42a-42f (e.g. multiplexing chambers 42a and 42f). It is contemplated to provide a semi-permeable membrane between outlets 74 of variable wells 64 and corresponding multiplexing chambers 42a-42f to prevent direct liquid mixing/cross-talk between via convective flow between variable wells 64 and corresponding multiplexing chambers 42a-42f.

In operation, it is intended for platform 26 to be utilized for the multiplex analysis of the interaction of three variables within a single chamber (e.g., multiplexing chambers 42a-42f). By way of example, multiplexing chambers 42a-42f may be filled through opening 51 with a desired media, such as a solution, gel, or the like. A fixed or first variable "experimentee" is loaded in common well 28 so as to pass into each multiplexing chamber 42a-42f though outlet 38 thereof. The fixed variable "experimentee" may take the form of a microbe, a cell species, a drug or antibiotic, a soluble factor or another factor. In addition, each variable well 64 may be loaded with a different "experimenting" variable which passes into the two multiplexing chambers 42a-42f with which outlet 74 of variable well 64 communicates. The different "experimenting" variables may take the form of various microbes, cells, drugs, antibiotics, soluble factors or other factors. In this way, a user may simply and easily observe the interaction of the experimentee and experimenting variables within each of the multiplexing chambers 42a-42f. It can be appreciated that platform 26 enables high-throughput screening of three interacting variables within a single multiplexing chamber 42a-42f at a time with simplicity in readout.

Further, it is noted that due to configuration of the plurality of multiplexing chambers 42a-42f, namely, the equilateral triangular configuration, the first, second and third vertices 52, 56 and 60, respectively, of each of the plurality of multiplexing chambers 42a-42f are an equal distance apart, thereby allowing for the variables loaded into common well 28 and variable wells 64 to contribute equally in terms of interaction distance therebetween. Since the triangle is the most basic unit that can define a planar surface, the interaction network may be scaled out in both the x and y dimensions, as compared to a linear 2-way interaction network which is confined to only one dimension at a time in terms of geometrical design. Further, by utilizing a triangular configuration, a multiplexing chamber 42a-42f may be joined to an adjacent multiplexing chamber 42a-42f along a single side thereof which, in turn, allows the two adjacent multiplexing chambers 42a-42f to share two wells, but have a single well isolated from the adjacent multiplexing chamber. This allows for a 3-factorial but single variable comparison between any two (2) neighboring triangular multiplexing chambers. It can be appreciated that microfluidic device 10 may be used to screen drug combinations that exert highest potency, find transcription factor combinations that show the highest stem cell differentiation efficiency, elucidate cell-cell or microbe interactions mechanisms, optimize chemical factors for cell culture, and multi-cell/organ drug metabolism.

By way of example, it can be understood that device 10 is amenable to solid culture and liquid culture or a combination of both. More specifically, for solid culture of prokaryotic cells (such as bacteria), variable wells 64 and multiplexing chambers 42a-42f may be filled with a warm agar solution including culture media (for example, Luria Broth (LB), Tryptic Soy Broth (TSB), Mueller Hinton Broth (MHB), or the like). The warm agar solution is allowed to solidify at room temperature or lower, e.g. 4° C. Device 10 filled with the agar solution can be stored for an extended period of time before use. Thereafter, bacteria may be inoculated by pipetting a bacteria solution onto the solid agar surface at opening 51 of a corresponding multiplexing chamber 42a-42f and thereafter cultured therein with device 10 facing either up or down. The experimenting variables such as drugs, antibiotics, other soluble factors or cells are added to device 10 via pipetting the solution on the solid agar surface at openings 70 of variable wells 64 and allowing the solution to absorb/diffuse therein.

For solid culture of eukaryotic cells (such as mammalian cells), variable wells 64 and multiplexing chambers 42a-42f can be filled as heretofore described with a hydrogel solution (such as collagen, matrigel, polyethylene glycol (PEG) gels, or the like) including culture media (such as Dulbecco's Modified Eagle's medium (DMEM), Roswell Park Memorial Institute medium (RPMI), or the like) and allowed to solidify to form a gel matrix. Cells may be premixed with the gel and loaded together into device 10 or seeded on top of the solidified gel matrix at opening 51 of a corresponding multiplexing chamber 42a-42f and/or openings 70 of variable wells 64.

For a mixed culture of eukaryotic cells and prokaryotic cells, a first portion of variable wells 64 may be loaded with eukaryotic cell-compatible gels such as collagen, matrigel, PEG gels, or the like, while a second portion of variable wells 64 may be loaded with prokaryotic cell-compatible gels such as agar. It is noted that for this "mixed gel" type of culture, one gel has to be fully solidified prior to adding the other gel to prevent the mixing thereof.

For a mixed solid and liquid co-culture system, either variable wells 64 or multiplexing chambers 42a-42f may be preloaded as heretofore described with a solid gel matrix prior to loading a liquid media in order to prevent direct liquid convection between variable wells 64. In other words, either variable wells 64 or multiplexing chambers 42a-42f can receive the solid gel matrix, but the solid gel matrix has to be loaded first and allowed to solidify prior to loading the liquid media. For example, for a solid prokaryotic cell co-culture with eukaryotic cells in liquid, variable wells 64 are first loaded with a solid agar gel, followed by adding liquid eukaryotic cell culture media into multiplexing chambers 42a-42f. The eukaryotic cells are then seeded into multiplexing chambers 42a-42 including liquid cell culture media, while the prokaryotic cells are seeded on top of the solid agar matrix at openings 70 in variable wells 64 and allowed to adhere.

It is noted that the experimenting variables such as drugs, antibiotics, other soluble factors can be added to variable wells 64 in a variety of ways. As noted above, if variable wells 64 are preloaded with a solid culture gel such as agar or collagen, then the experimenting variable can be added on top of the solid culture gel at opening 70 of a corresponding variable well 64 and allowed to absorb or diffuse into the solid culture gel. Alternatively, an experimenting variable or variables may be mixed with the liquid gel solution prior to loading in a corresponding variable well 64. Thereafter, the mixture may be loaded into the corresponding variable well 64. The experimenting variable-infused gels can be stored for an extended period of time without cross-contamination/mixing as long as the corresponding multiplexing chambers 42a-42f are left empty and not filled with liquid or solid media. In this manner, diffusion of the experimenting variable into the corresponding multiplexing chamber 42a-42f is only initiated upon the adding of liquid/solid media into the corresponding multiplexing chamber 42a-42f.

If variable wells 64 are filled with a liquid media/reagent such as phosphate-buffered saline (PBS), LB or DMEM, the experimenting variables may be added to a corresponding variable well 64 by pipetting the experimenting variables into the liquid media. However, such liquid media are less amenable to long term storage and transportation when received with device 10. In order to overcome this limitation, the liquid media and/or the experimenting variables may be dried by desiccation or lyophilization inside device 10 after loading. After drying, the dried liquid media inside variable wells 64 can be stored for an extended period of time without cross-contamination/mixing therebetween as long as corresponding multiplexing chambers 42a-42f are left empty and not filled with a liquid or a solid media. To "re-activate" the dried liquid media, water or other liquid/solid media solutions may be added to a corresponding variable well 64 to re-dissolve the liquid media therein. As described above, diffusion into multiplexing chambers 42a-42f is only initiated upon the filing of multiplexing chambers 42a-42f with a liquid/solid media.

It is contemplated to affix a removable membrane to upper surface 22 of base 12 which overlaps openings 70 to variable wells 64 to isolate the media inside variable wells 64 from the external embodiment during storage. Similarly, a removable membrane may be affixed to lower surface 24 of base 12 which overlaps openings 51 to multiplexing chambers 42a-42f to further isolate the dried liquid media inside variable wells 64 from the external embodiment during storage.

Figure 2A:
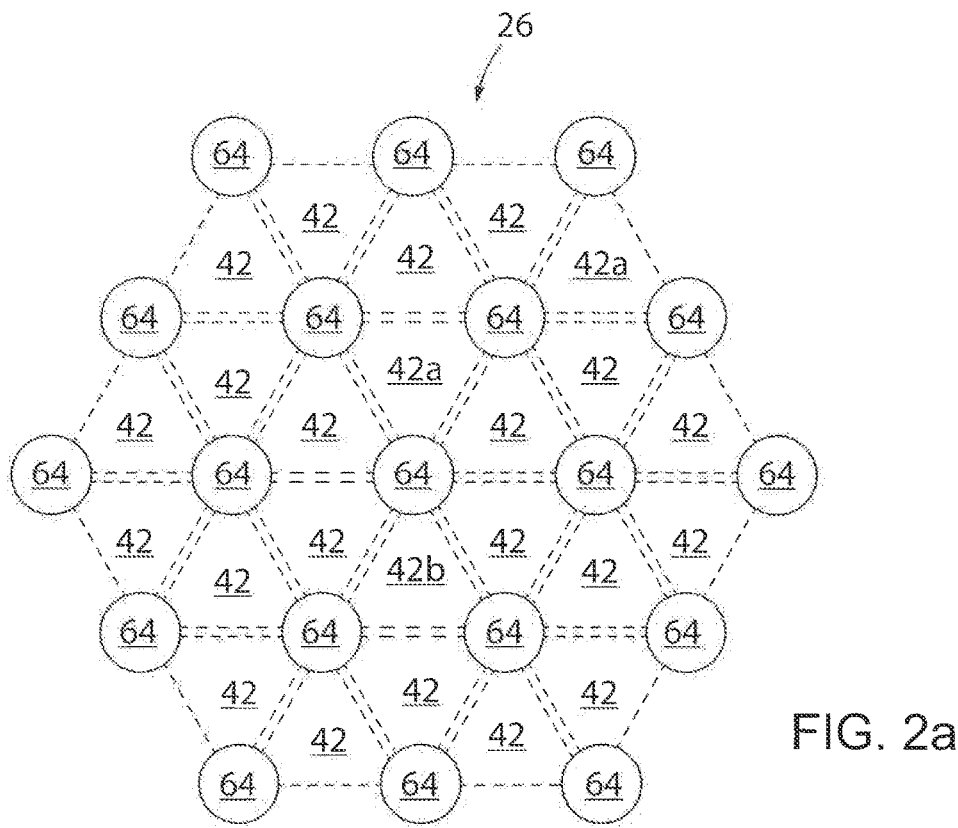
FIG. 2a is a schematic, top plan view of the microfluidic device of FIG. 1 expanded to include an increased higher number of multiplexing chambers.
Figure 2B:
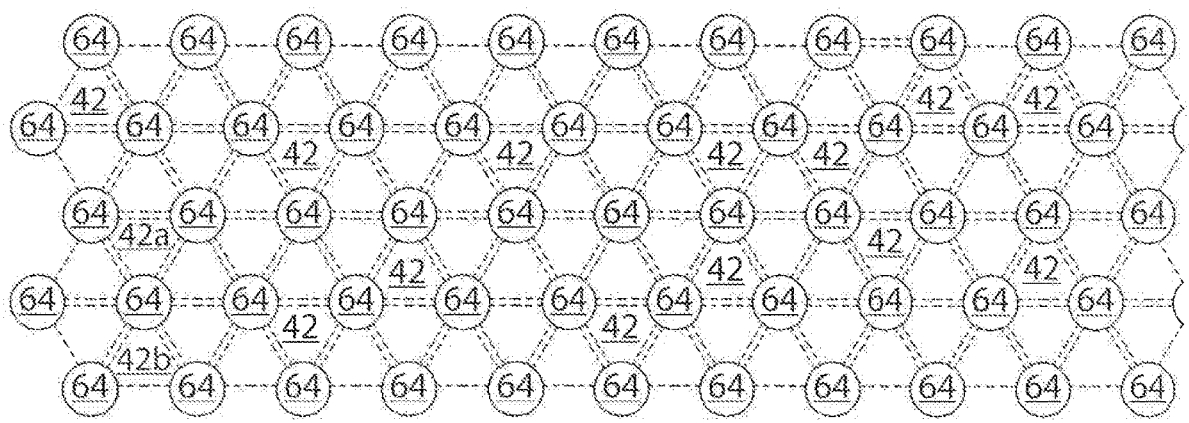
FIG. 2b is a schematic, top plan view of the microfluidic device of FIG. 1 expanded in a single direction to include an increased higher number of multiplexing chambers.

Referring to FIGS. 2a-2b, using the design principles of the microfluidic device 10 described above, it can be appreciated that the scale of platform 26 may be expanded to include a higher number of variable wells 64 and multiplexing chambers, generally designated by the reference numeral 42. By way of example, platform 26 may be expanded to provide for a scaled-out symmetrical hexagonal design, FIG. 2a or scaled-out in a single direction, FIG. 2b. It can be appreciated that multiplexing chambers 42 are identical in structure to microfluidic chambers 42a-42f, and as such, the prior description of microfluidic chamber 42a is understood describe multiplexing chamber 42 as if fully described herein. The choice of the configuration depends on the scale of the experiment (number of combinations required) and the distance of interactions in question.

Figure 7:
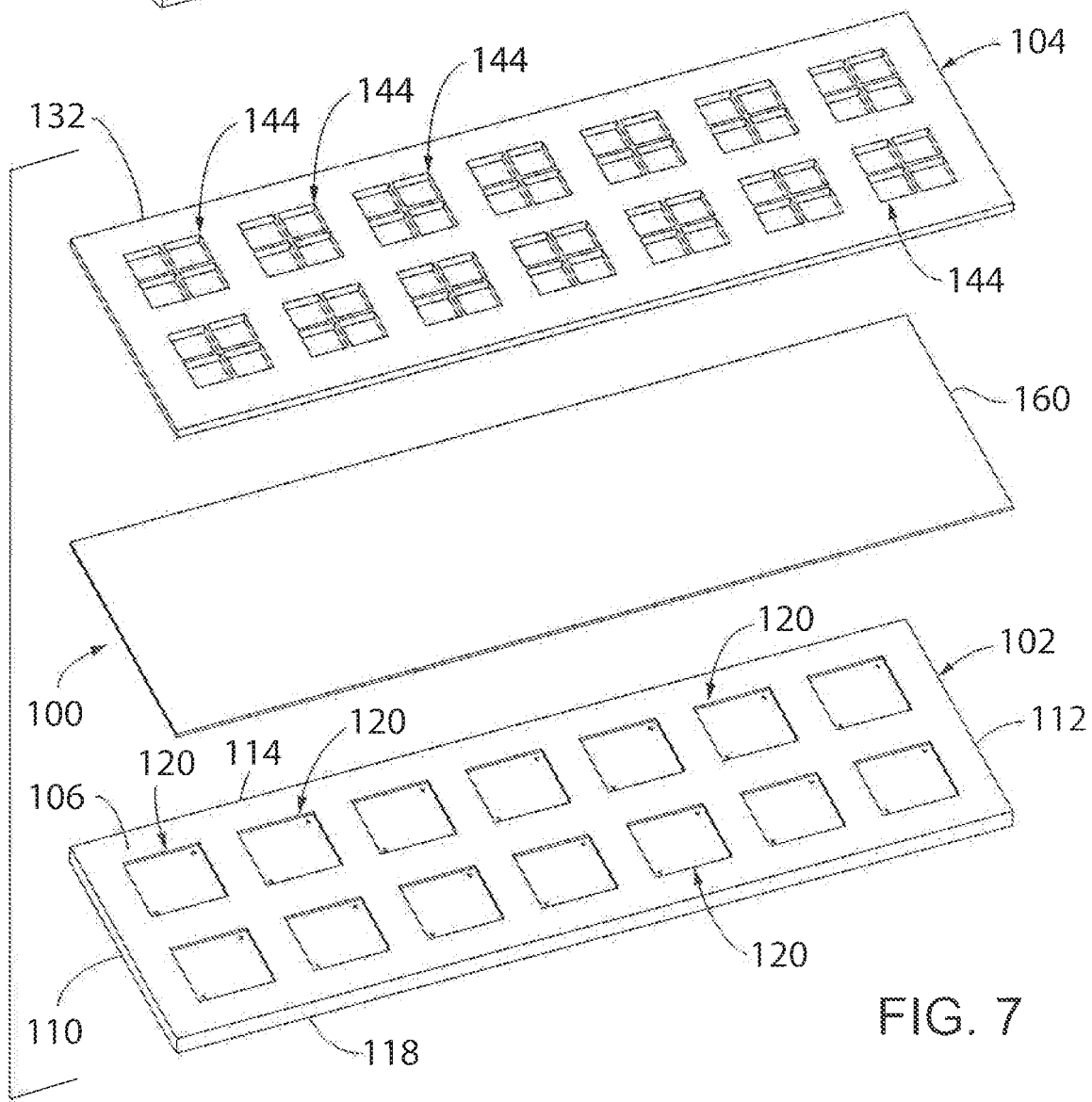
FIG. 7 is an exploded view of the microfluidic device of FIG. 6.
Figure 8:
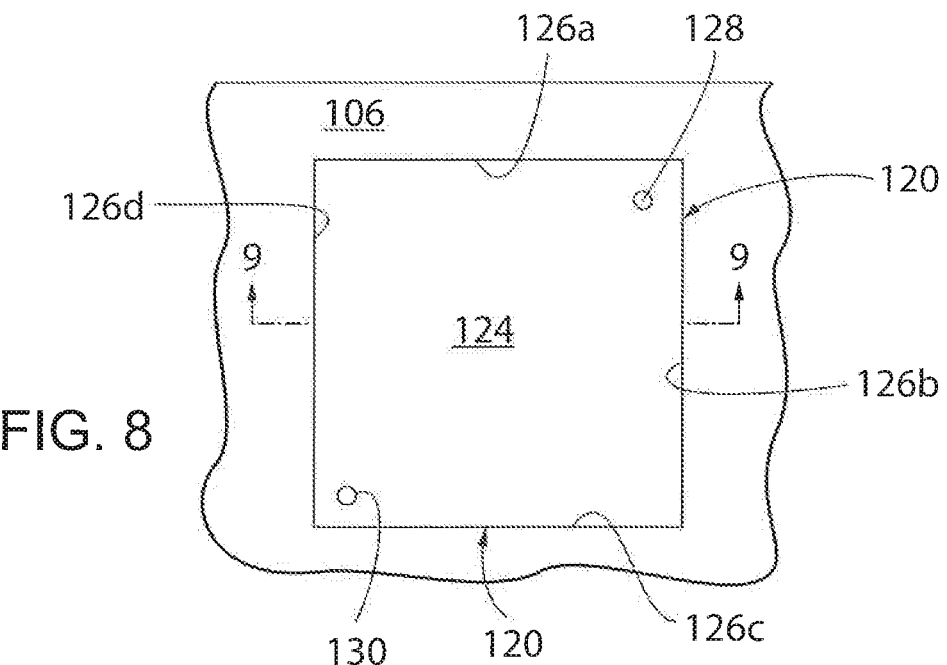
FIG. 8 is a top plan view of a first layer of the microfluidic device of FIG. 6.
Figure 9:
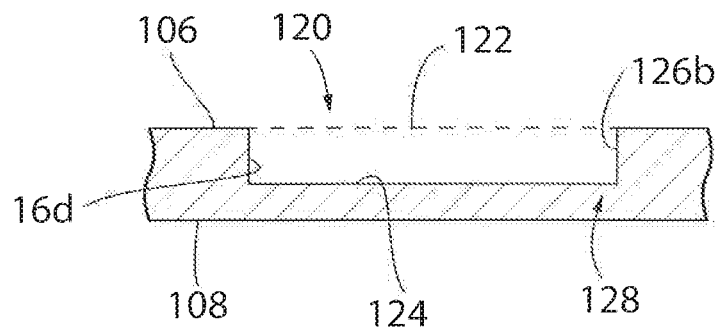
FIG. 9 is a cross-sectional view of the first layer of the microfluidic device taken along line 9-9 of FIG. 8.

Referring to FIG. 7, an alternate embodiment of a microfluidic device in accordance with the present invention is generally designated by the reference numeral 100. As hereinafter described, microfluidic device 100 incorporates multiple platforms 101 for testing the antibiotic sensitivity of a polymicrobial infection. Microfluidic device 100 includes first and second layers 102 and 104, respectively, FIG. 7. Referring to FIGS. 7-9, first layer 102 is formed from a polymeric material (e.g., polystyrene) and includes upper and lower surfaces 106 and 108, respectively, interconnected by first and second ends 110 and 112, respectively, and first and second sides 114 and 118, respectively. A plurality of wells 120 are provided in upper surface 106. In the depicted embodiment, the plurality of wells 120 are arranged in two rows and seven columns. However, the number and arrangement of the plurality of wells 120 in upper surface 106 of first layer 102 may be varied without deviating from the scope of the present invention.

Each of the plurality of wells 120 includes an opening 122 communicating with upper surface 106 of first layer 102 and is defined by a generally planer lower surface 124 spaced from upper surface 106 of first layer 102 by a sidewalls 126a-126d and generally parallel to lower surface 108 of first layer 102. In the depicted embodiment, sidewalls 126a-126d have identical depths D and identical widths W. However, the depths and widths of sidewalls 126a-126d may be varied without deviating from the scope of the present invention. In addition, sidewall 126a and sidewall 126c are generally parallel to each other and perpendicular to sidewalls 126b and 126d. Similarly, sidewall 126b and sidewall 126d are generally parallel to each other and perpendicular to sidewalls 126a and 126c. As described, well 120 has a generally square configuration in cross-section. A media inlet 128 extends between lower surface 124 of each of the plurality of wells 120 and lower surface 108 of first layer 102 at a location adjacent the intersection of sidewalls 126a and 126b. In addition, an air outlet 130 extends between lower surface 124 of the plurality of wells 120 and lower surface 108 of first layer 102 at a location adjacent the intersection of sidewalls 126a and 126b.

Figure 9A:
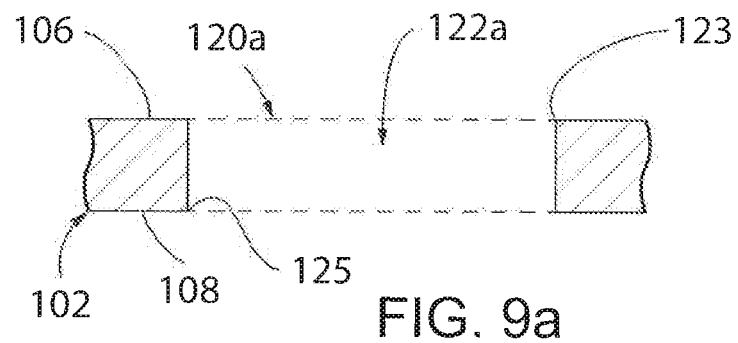

Referring to FIG. 9a, an alternate construction of the plurality of wells in first layer 102 is generally designated by the reference numeral 120a. Each of the plurality of wells 120a includes an opening 122a extending through first layer 102. Opening 122a has a first end 123 communicating with upper surface 106 of first layer 102 and a second end 125 communicating with lower surface 108 of first layer 102. Sidewalls 127a-127d define opening 122a and are generally perpendicular to upper and lower surfaces 106 and 108, respectively, of first layer 102. It is contemplated for sidewalls 127a-127d have identical depths D and identical widths W. However, the depths and widths of sidewalls 127a-127d may be varied without deviating from the scope of the present invention. In addition, sidewall 127a and sidewall 127c are generally parallel to each other and perpendicular to sidewalls 127b and 127d. Similarly, sidewall 127b and sidewall 127d are generally parallel to each other and perpendicular to sidewalls 127a and 127c. As described, each of the plurality of wells 120a has a generally square configuration in cross-section.

Figure 10:
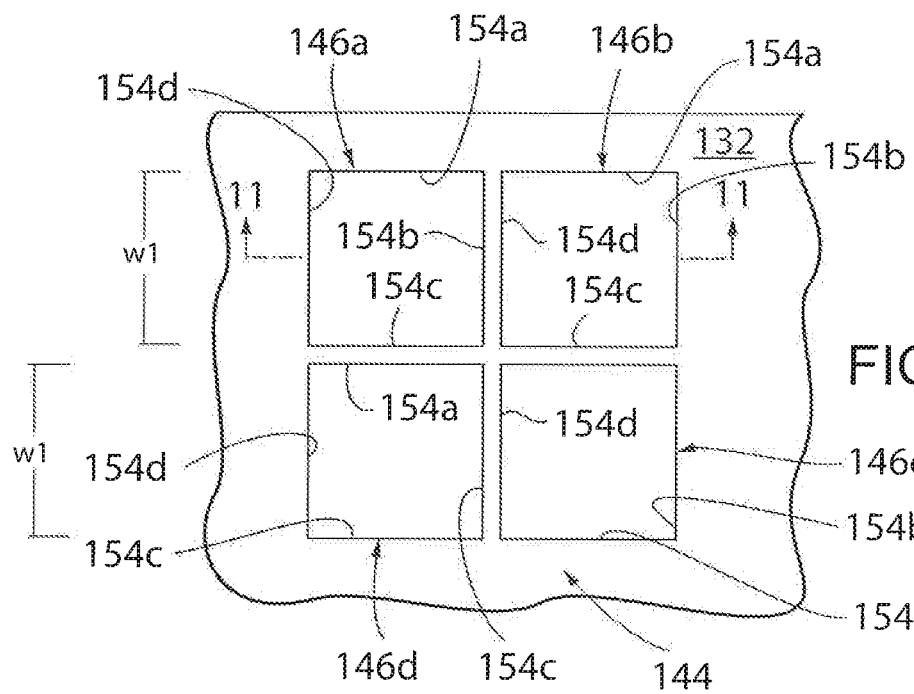
FIG. 10 is a top plan view of a second layer of the microfluidic device of FIG. 6.
Figure 11:
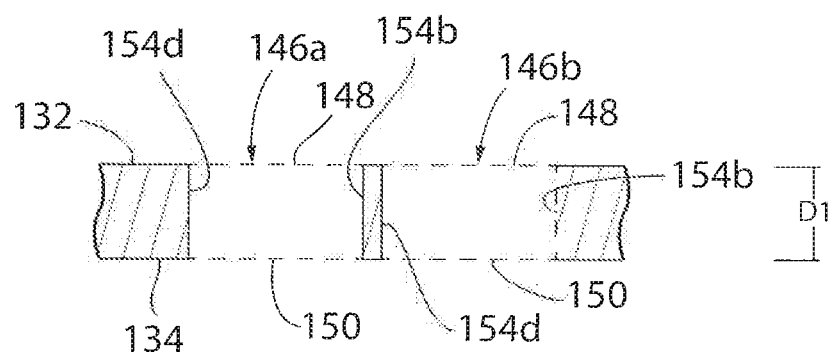
FIG. 11 is a cross-sectional view of the second layer of the microfluidic device taken along line 11-11 of FIG. 10.

Referring to FIGS. 7 and 10-11, second layer 104 is formed from a polymeric material (e.g., polystyrene) and includes upper and lower surfaces 132 and 134, respectively, interconnected by first and second ends 136 and 138, respectively, and first and second sides 140 and 142, respectively. A plurality of sets 144 of chambers 146a-146d extend through second layer 104 between the upper and lower surfaces 132 and 134, respectively, thereof. It is in intended for the number of the plurality of sets 144 of chambers 146a-146d in second layer 104 to correspond to the number of the plurality of wells 120 in upper surface 106 of first layer 102. As such, in the depicted embodiment, the plurality of sets 144 of chambers 146a-146d are arranged in two rows and seven columns.

In the depicted embodiment, each set 144 of chambers 146a-146d includes four chambers 146a-146d of identical configuration and proportion arranged in two rows and two columns. However, the number and configuration of chambers 146a-146d may be varied, as desired. Further, in view of the foregoing, it can be understood that the description of chamber 146a hereinafter provided describes chambers 146b-146d as if fully described herein. Chamber 146a includes an upper opening 148 communicating with upper surface 132 of second layer 104 and a lower opening 150 communication with lower surface 134 of second layer 104. Sidewalls 154a-154d extending between upper surface 132 and lower surface 134 of second layer 104 so as to define chamber 146a. Sidewalls 154a-154d have identical depths D1 and identical widths W1. In addition, sidewall 154a and sidewall 154c are generally parallel to each other and perpendicular to sidewalls 154b and 154d. Similarly, sidewall 154b and sidewall 154d are generally parallel to each other and perpendicular to sidewalls 154a and 154c.

In order to construct platform 101 of microfluidic device 100, first and second layers 102 and 104, respectively, are positioned such that lower surface 134 of second layer 104 is directed at upper surface 106 of first layer 102, FIG. 7. Permeable membrane 160 is positioned between lower surface 134 of second layer 104 is directed at upper surface 106 of first layer 102. By way of example, permeable membrane 160 may take the form of a 0.2 micrometer (μm) porous polycarbonate membrane. Thereafter, first and second layers 102 and 104, respectively, are bonded together in any conventional manner such that first and second ends 136 and 138, respectively, and first and second sides 140 and 142, respectively, of second layer 104 are aligned with first and second ends 110 and 112, respectively, and first and second sides 114 and 118, respectively, of first layer 102, thereby capturing permeable member 160 therebetween.

Figure 8A:
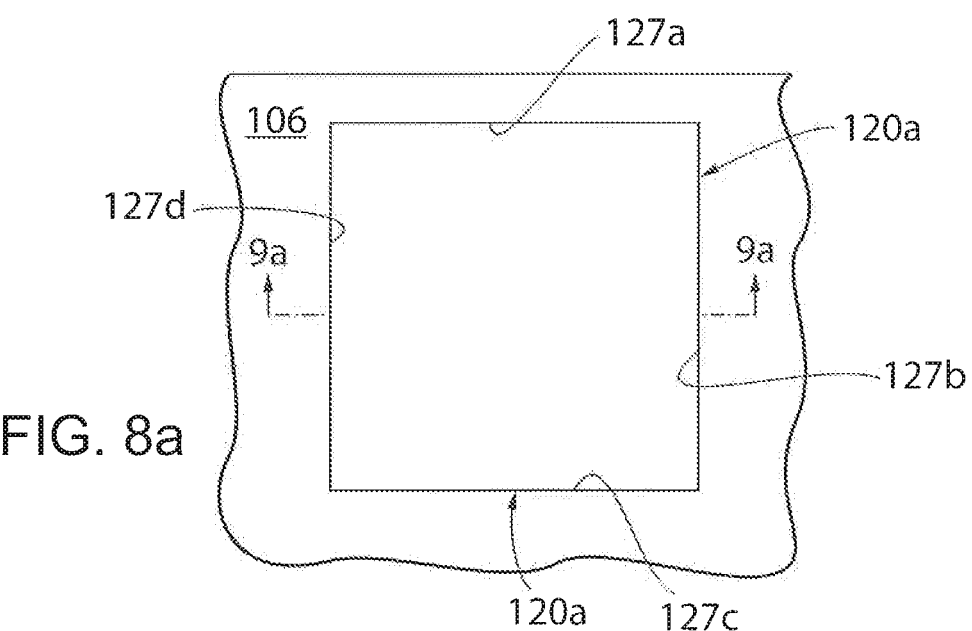
FIG. 8a is a top plan view of an alternate construction of a first layer of the microfluidic device of FIG. 6.

With first and second layers 102 and 104, respectively, bonded together as heretofore described, each set 144 of chambers 146a-146d is aligned with a corresponding one of the plurality of wells 120, FIGS. 6 and 12a-12d, or alternatively, with one of the plurality of wells 120a, FIGS. 8a and 9a. With each set 144 of chambers 146a-146d aligned with a corresponding one of the plurality of wells 120, sidewalls 154a of chambers 146a and 146b of each set 144 of chambers 146a-146d are generally co-planar with sidewall 126a of a corresponding well 120 of each of the plurality of wells 120; sidewalls 154b of chambers 146b and 146c of each set 144 of chambers 146a-146d are generally co-planar with sidewall 126b of a corresponding well 120 of each of the plurality of wells 120; sidewalls 154c of chambers 146c and 146d of each set 144 of chambers 146a-146d are generally co-planar with sidewall 126c of a corresponding well 120 of each of the plurality of wells 120; and sidewalls 154d of chambers 146d and 146a of each set 144 of chambers 146a-146d are generally co-planar with sidewall 126d of a corresponding well 120 of each of the plurality of wells 120. Permeable member 160 separates each set 144 of chambers 146a-146d for a corresponding well 120 of each of the plurality of wells 120.

Alternatively, with each set 144 of chambers 146a-146d is aligned with a corresponding one of the plurality of wells 120a, sidewalls 154a of chambers 146a and 146b of each set 144 of chambers 146a-146d are generally co-planar with sidewall 127a of a corresponding well 120a of each of the plurality of wells 120a; sidewalls 154b of chambers 146b and 146c of each set 144 of chambers 146a-146d are generally co-planar with sidewall 127b of a corresponding well 120a of each of the plurality of wells 120a; sidewalls 154c of chambers 146c and 146d of each set 144 of chambers 146a-146d are generally co-planar with sidewall 127c of a corresponding well 120a of each of the plurality of wells 120a; and sidewalls 154d of chambers 146d and 146a of each set 144 of chambers 146a-146d are generally co-planar with sidewall 127d of a corresponding well 120a of each of the plurality of wells 120a. Permeable member 160 separates each set 144 of chambers 146a-146d for a corresponding well 120a of each of the plurality of wells 120a.

In operation, different microbes are provided in each chamber 146a-146d of each set 144 of chambers 146a-146d. The microbes may take the form of bacteria, viruses, fungi, yeasts, parasites, antibiotics or a combination thereof. By way of example, different bacterial strains (e.g., bacterial strains 162 and 164 in FIGS. 12a-12d) may be provided or cultured in media 166 in each chamber 146a-146d of each set 144 of chambers 146a-146d. For example, a small volume (10 μL) of four samples of bacterial strains from the same patient may be provided or cultured individually in each chamber 146a-146d. Permeable membrane 160 is specifically chosen so that media 166 from chambers 146a-146d of each set 144 of chambers 146a-146d does not flow through permeable membrane 160 into a corresponding well 120 or 120a when the corresponding well 120 or 120a is empty (in other words, filled with air), FIGS. 12a and 12b. When utilizing the plurality of wells 120, each of the plurality of wells 120 may be filled through media inlets 128 with different medias, e.g., different antibiotic medias, collectively designated by the reference numeral 168, FIG. 12c. It can be appreciated that microfluidic device 100 may be flipped upside down to facilitate filling of the plurality of wells 120 given that the surface tension of media 166 in chambers 146a-146d of each set 144 of chambers 146a-146d retains media 166 therein. Alternatively, wherein utilizing the plurality of wells 120a, each of the plurality of wells 120a may be filled through second end 125 of opening 122a with different medias, e.g., different antibiotic medias, as heretofore described. It can be appreciated that microfluidic device 100 may be flipped upside down to facilitate filling of the plurality of wells 120a given that the surface tension of media 166 in chambers 146a-146d of each set 144 of chambers 146a-146d retains media 166 therein.

Once the plurality of wells 120 or 120a with different medias 168 (e.g., different antibiotic therapies), each of the plurality of wells 120 or 120a serves as a liquid pool that fluidically connects each of chambers 146a-146d of a corresponding set 144 of chambers 146a-146d through permeable membrane 160. For example, with well 120 filled with media 168, bacteria 162 and 164 in chambers 146a-146d of the corresponding set 144 of chambers 146a-146d will be in soluble factor contact through diffusion, FIG. 12d. The structure of permeable membrane 160 is intended to be efficient in preventing bacteria migration, while providing sufficiently fast diffusion. By analyzing the different media 168 in each of the plurality of wells 120 or 120a, the susceptibility of the combination of specific bacterial pathogens cultured in chambers 146a-146d to various antibiotic therapies provided in the plurality of wells 120 or 120a may be simply and easily assessed.

As described, microfluidic device 100 allows for the simultaneous testing of various antibiotic therapies to be performed on a combination of specific microbes provided in sets 144 of chambers 146a-146d. It can be understood that the number of chambers in each set 144 of chambers 146a-146d may be increased or decreased to correspond to the number of microbes in a desired combination. Further, it can be appreciated the open-microfluidic nature enables unique advantages in accessibility, allowing the microbes, e.g. bacteria 162 and 164, to be easily recollected for traditional antibiotic sensitivity or antibiotic susceptibility measures or biofilm assessment.

Further, it is contemplated to pre-load the plurality of wells 120 or 120a with a selected antibiotic so as to provide microfluidic device 100 as a pre-packaged kit to test different microbes, e.g., gram negative and positive bacteria, thereagainst. For example, the plurality of wells 120 or 120a may be preloaded with: penicillins, including amoxicillin+/–clavulanate, ampicillin+/–sulbactam, and piperacillin+/–tazobactam; cephalosporins, including cefepime, cefoxitin, cefazolin, and ceftriaxone; carbapenems, including meropenem and ertapenem; monobactams, including aztreonam; fluoroquinolones, including ciprofloxacin; aminoglycosides, including gentamicin; macrolides, including azithromycin; and others, including vancomycin, clindamycin, rifampin, trimethoprim+/–sulfamethoxazole and tetracycline. A removable membrane may be affixed lower surface 108 of first layer 102 of which overlaps openings 122a of the plurality of wells 120a to isolate the media within the plurality of wells 120a from the external embodiment during storage. Similarly, a removable membrane may be affixed to upper surface 132 of second layer 104 which overlaps openings 148 of chambers 146a-146d to further isolate the media inside the plurality of wells 120 or 120a from the external embodiment during storage. When using the microfluidic device 100, any removable membranes affixed thereto may be removed thereby allowing a user to load different microbes in each chamber 146a-146d of each set 144 of chambers 146a-146d, as heretofore described, to test the gram negative and positive bacteria against the pre-loaded antibiotic.

Various modes of carrying out the invention are contemplated as being within the scope of the following claims particularly pointing out and distinctly claiming the subject matter, which is regarded as the invention.

We claim:

1. A platform for testing antibiotic sensitivity of a polymicrobial infection, comprising:
    a body defining:
    a first plurality of chambers, each chamber of the first plurality of chambers being adapted for receiving a corresponding microbe of the polymicrobial infection therein;
    a first well having a plurality of outlets, each outlet in fluidic communication with a corresponding chamber of the first plurality of chambers, the first well adapted for receiving a first selected antibiotic therapy therein;
    a second plurality of chambers, each chamber of the second plurality of chambers being adapted for receiving a corresponding microbe of the polymicrobial infection therein; and
    a second well having a plurality of outlets, each outlet in fluidic communication with a corresponding chamber of the second plurality of chambers, the second well adapted for receiving a second selected antibiotic therapy therein;
    wherein:
    the first selected antibiotic therapy received in the first well fluidically connects each of the first plurality of chambers such that microbes received in the first plurality of chambers are in soluble factor contact;
    the second selected antibiotic therapy received in the second well fluidically connects each of the second plurality of chambers such that microbes received in the second plurality of chambers are in soluble factor contact;
    a first chamber is one of the first plurality of chambers and one of the second plurality of chambers, such that the first well and the second well are in fluid communication with the first chamber;
    the first chamber shares a partition wall with one of the first plurality of chambers and one of the second plurality of chambers;
    the body includes upper and lower surfaces, each of the first and second plurality of chambers having an opening communicating with the upper surface of the body; and
    the first well is partially defined by a closed surface within the body, the closed surface being generally parallel to the lower surface of the body.

2. The platform of claim 1 wherein the body further includes a well inlet extending between the closed surface of the first well and the lower surface of the body, the well inlet allowing for access to the first well for loading the selected antibiotic therapy therein.

3. The platform of claim 2 wherein the body further includes an air outlet extending between the closed surface of the first well and the lower surface of the body, the air outlet allowing for the purging of air from the first well during the loading of the selected antibiotic therapy therein.

4. A platform for testing antibiotic sensitivity of a polymicrobial infection, comprising:
    a body defining:
    a plurality of sets of chambers, each set of chambers having a plurality of chambers adapted for receiving microbes of the polymicrobial infection therein; and
    a plurality of wells, each well:
    associated with a corresponding set of chambers of the plurality of sets of chambers;
    having an input in fluidic communication with each chamber of the plurality of chambers in the corresponding set of chambers; and
    being adapted for receiving a selected antibiotic therapy therein;
    wherein:
    a chamber of the plurality of chambers of a first set of chambers of the plurality of sets of chambers is one of the plurality of chambers of a second set of chambers of the plurality of sets of chambers; and
    the selected antibiotic therapy received in the well associated with a corresponding set of chambers fluidically connects the plurality of chambers in the corresponding set of chambers such that microbes received in the plurality of chambers in the corresponding set of chambers are in soluble factor contact.

5. The platform of claim 4 wherein the body further includes a permeable membrane disposed between the outlets of the plurality of chambers of the plurality of sets of chambers and the inputs of corresponding wells of the plurality of wells.

6. The platform of claim 5 wherein the permeable membrane is a porous polycarbonate membrane.

7. The platform of claim 4 wherein the body includes upper and lower surfaces, each of the plurality of chambers of the plurality of sets of chambers has an opening communicating with the upper surface of the body.

8. The platform of claim 7 wherein each well of the plurality of wells is partially defined by a closed surface within the body, the closed surface being generally parallel to the lower surface of the body.

9. The platform of claim 8 wherein the body further includes a plurality of well inlets, each well inlet:
    extending between the closed surface of a corresponding well and the lower surface of the body; and
    allowing for access to the corresponding well for loading the selected antibiotic therapy therein.

10. The platform of claim 8 wherein the body further includes a plurality of air outlets, each air outlet:
    extending between the closed surface of the corresponding well and the lower surface of the body; and
    allowing for the purging of air from the corresponding well during the loading of the selected antibiotic therapy therein.

* * * * *